(12) United States Patent
Conover

(10) Patent No.: US 7,311,900 B2
(45) Date of Patent: Dec. 25, 2007

(54) GEL/AIR FRESHENER SYSTEM

(75) Inventor: Donald Conover, Buffalo Grove, IL (US)

(73) Assignee: Belle-Aire Fregrances, Inc., Mundelein, IL (US)

( * ) Notice: Subject to any disclaimer, the term of this patent is extended or adjusted under 35 U.S.C. 154(b) by 286 days.

(21) Appl. No.: 11/037,278

(22) Filed: Jan. 18, 2005

(65) Prior Publication Data

US 2005/0175578 A1    Aug. 11, 2005

Related U.S. Application Data

(60) Provisional application No. 60/548,244, filed on Feb. 27, 2004, provisional application No. 60/543,581, filed on Feb. 11, 2004.

(51) Int. Cl.
| | |
|---|---|
| *A61L 9/01* | (2006.01) |
| *A61L 9/00* | (2006.01) |
| *A61L 9/04* | (2006.01) |
| *A61K 61/14* | (2006.01) |
| *A61K 61/695* | (2006.01) |

(52) U.S. Cl. .................. 424/76.1; 424/489; 424/76.2; 424/76.3; 514/63

(58) Field of Classification Search ............... 424/489, 424/76.1, 76.2, 76.3, 724; 514/63
See application file for complete search history.

(56) References Cited

U.S. PATENT DOCUMENTS

| | | | |
|---|---|---|---|
| 3,576,760 | A | 4/1971 | Gould et al. |
| 4,020,156 | A | 4/1977 | Murray et al. |
| 4,561,997 | A | 12/1985 | Roehl |
| 5,081,104 | A | 1/1992 | Orson, Sr. |
| 5,788,155 | A | 8/1998 | Martin et al. |
| 6,352,210 | B1 | 3/2002 | Requejo |
| 6,435,423 | B2 | 8/2002 | Hurry et al. |
| 6,448,219 | B1 | 9/2002 | Cooper |
| 6,478,440 | B1 | 11/2002 | Jaworski et al. |
| 6,569,387 | B1 | 5/2003 | Furner et al. |
| 6,610,254 | B1 | 8/2003 | Furner et al. |
| 6,631,852 | B1 | 10/2003 | O'Leary |
| 2002/0041860 | A1 | 4/2002 | Requejo |
| 2002/0155087 | A1 | 10/2002 | Ryan et al. |
| 2003/0097936 | A1 | 5/2003 | Maleeny et al. |
| 2003/0168521 | A1 | 9/2003 | Skalitzky et al. |
| 2004/0094037 | A1 | 5/2004 | Maleeny et al. |

*Primary Examiner*—Johann R. Richter
*Assistant Examiner*—Konata M. George
(74) *Attorney, Agent, or Firm*—Schiff Hardin LLP

(57) ABSTRACT

A powder mixture for mixing with water to form a gel for a gel/air freshener system includes a fragrance, amorphous fumed silica, a super-absorbent polymer and a surfactant. The mixture can also include a dye and a deodorizer, which may replace a portion of the fragrance or be in combination with the fragrance.

7 Claims, No Drawings

GEL/AIR FRESHENER SYSTEM

CROSS-REFERENCE TO RELATED APPLICATIONS

This application claims benefit from the filing date of U.S. Provisional Application Ser. No. 60/543,581, filed Feb. 11, 2004, and U.S. Provisional Application Ser. No. 60/548,244, filed Feb. 27, 2004.

BACKGROUND OF THE INVENTION

The present invention is directed to a mixture of powders which, with the addition of water, will form a gel which will introduce a fragrance and/or act as air freshener deodorizer.

To either add a fragrance to a room or to provide an air freshener, it is common to provide either the fragrance or deodorizer in the form of a gel. The gel will give off either a scent to mask undesirable odors, which may be smoke or cooking odors, or a deodorizer to remove the undesirable odors. In addition to using gels, which will add fragrance or freshen the air, it is also known to provide a wick arrangement which extends into a liquid which is either the fragrance, air freshener or deodorizer.

SUMMARY OF THE INVENTION

An object of the present invention is to provide a mixture of dry powders which will form a gel with the addition of water. This mixture includes a fragrance; amorphous fumed silica which can be a synthetic amorphous silicon dioxide which is crystalline free; super-absorbent polymer having a chemical name such as sodium polyacrylate, a surfactant, for example sodium dodecylbenzene sulfonate; a dye in a liquid to add color to the powder mixture and any resulting gel; and a deodorizer. It has been found that the air freshener material can be a gel that is sold in sealed cups or it can be sold in a powder form to which the purchaser will add water to cause the gelling. An advantage of selling it in the dry form in which the purchaser adds water is that there is a reduced transportation cost for not transporting the liquid from place to place.

DESCRIPTION OF THE PREFERRED EMBODIMENTS

The principles of the present invention are particularly useful in a mixture of powder which, when water is added, will form a gel for introducing fragrance or to act as an air freshener or deodorizer. A general formula for the dry powders which would form a gel includes the following ranges:

| | |
|---|---|
| 0–60% | fragrance; |
| 5–25% | amorphous fumed silica which can be a synthetic amorphous silicon dioxide which is crystalline free; |
| 10–68% | super-absorbent polymer having a chemical name of sodium polyacrylate; |
| .05–18% | surfactant for example sodium dodecylbenzene sulfonate; |
| 0–10% | dye in a liquid to add color to the powder and gel; and |
| 0–10% | deodorizer; and |
| 10–60% | combination of the fragrance and the deodorizer. |

Another useful range for the mixtures is the following range:

| | |
|---|---|
| 0–50% | fragrance; |
| 5–30% | amorphous fumed silica; |
| 10–50% | super-absorbent polymer; |
| .05–15% | surfactant; |
| 0–5% | dye in a liquid; |
| 0–10% | deodorizer; and |
| 20–50% | combination of the fragrance and the deodorizer. |

The fragrances can be those sold by Belle-Aire Fragrances, Inc. and can have different scents. For example, it can be a fruit scent, such as apples, oranges, limes or the scents of flowers. The dyes can also be color-coded to the fragrance. For example, if the fragrance is a lime, then the dye can have a lime-green color.

The amorphous fumed silica, which is sold by Cabot Corporation under the Trademark Cab-O-Sil, has proven to be effective to absorb the liquid fragrances, deodorizer and any liquid dyes. The Cab-O-Sil will be in a form of a fine particle with a size similar to flour.

For a surfactant, a product sold under the Trademark NACCONOL 90G by Stepan Company has proven to be an extremely effective surfactant.

For the sodium polyacrylates, a mixture of a coarse and fine polyacrylates has proven effective for the super absorbent polymer. For example, a mixture of sodium polyacrylate sold under the Trademark NORSOCRYL-60 as the coarse powder and NORSOCRYL XFS as the fine powder have proven very effective. Both of these can be obtained from Emerging Technologies, Inc.

As mentioned above, the mixture of powder can be shipped in the dry form with the customer adding water to cause the gelling and the release of the fragrance. It is also possible to add water before shipping, so that the gel is shipped in sealed containers and the customer does not need to add water to get the gel.

As mentioned above in the two different ranges, I have found a good result with the following specific general formula of:

| | |
|---|---|
| 37.50% | Belle-Aire Fragrance; |
| 12.5% | Cab-O-Sil; |
| 37.50% | coarse sodium polyacrylate (NOROCRYL-60); |
| 5% | fine sodium polyacrylate (NORSOCRYL XFS); |
| 3.75% | surfactant; |
| 3.75% | Dye (1% in water). |

As mentioned earlier in the various ranges, an alternative formula for deodorizing purposes could be the same as above with the addition of 1-10% level of a deodorizer, such as sold under the Trademark ORDENONE by Belle-Aire Fragrance, Inc. This deodorizer can replace a like portion of the fragrance or completely replace the fragrance.

Although various minor modifications may be suggested by those versed in the art, it should be understood that I wish to embody within the scope of the patent granted hereon all such modifications as reasonably and properly come within the scope of my contribution to the art.

I claim:

1. A powder mixture which, when water is added, will form a gel/air freshener system, said mixture consisting essentially of a range of 5 to 60% fragrance, 5 to 25% amorphous fumed silica, 10 to 68% super-absorbent polymer, where the super-absorbent polymer is a sodium polyacrylate, 0.05 to 18% surfactant, where the surfactant is a sodium dodecylbenzene sulfonate, 0.20 to 10% dye in a liquid to add color, and 0.20 to 10% deodorizer with a combination of the fragrance and deodorizer being 10 to 60%.

2. A powder mixture according to claim 1, wherein the amorphous fumed silica is a synthetic amorphous silicon dioxide which is crystalline-free.

3. A powder mixture according to claim 2, wherein the fragrance is 37.50%; the amorphous silicon dioxide is 12.5%; the super-absorbent polymer is 37.5% of a coarse polymer and 5% of a fine polymer; the surfactant is 3.75% and the dye is 3.75%.

4. A powder mixture according to claim 3, wherein 1 to 10% of the fragrance is replaced by a deodorizer.

5. A powder mixture for forming a gel when water is added, said mixture consisting essentially of a range of 5 to 60% fragrance, 0.20 to 10% deodorizer, 5 to 25% amorphous fumed silica, 10 to 68% super-absorbent polymer, where the super-absorbent polymer is a sodium polyacrylate, 0.05 to 18% surfactant, where the surfactant is a sodium dodecylbenzene sulfonate, 0.20 to 10% dye in a liquid to add color and a combination of the fragrance and deodorizer being in a range of 10 to 50%.

6. A powder mixture according to claim 5, wherein the amorphous fumed silica is a synthetic amorphous silicon dioxide which is crystalline-free.

7. A powder mixture according to claim 6, wherein the fragrance is 37.5%, amorphous silicon dioxide is 12.5%, the super-absorbent polymer is formed by 37.5% of a coarse sodium polyacrylate and 5% of a fine sodium polyacrylate, the surfactant is 3.75% and the dye is 3.75%.

* * * * *